United States Patent [19]

Ericsson

[11] 4,339,434
[45] Jul. 13, 1982

[54] METHOD OF INCREASING THE INCIDENCE OF FEMALE OFFSPRING

[75] Inventor: Ronald J. Ericsson, Sausalito, Calif.

[73] Assignee: Gametrics Limited, Sausalito, Calif.

[21] Appl. No.: 293,079

[22] Filed: Aug. 17, 1981

[51] Int. Cl.³ .............................................. A61K 35/48
[52] U.S. Cl. .................................... 424/105; 128/1 R
[58] Field of Search ........................ 424/105; 128/1 R

[56] References Cited

U.S. PATENT DOCUMENTS 4,009,260  2/1977  Ericsson ............................. 424/105
4,085,205  4/1978  Hancock ............................ 424/105
4,225,405  9/1980  Lawson ............................. 424/105

*Primary Examiner*—Sam Rosen
*Attorney, Agent, or Firm*—Millen & White

[57] ABSTRACT

The likelihood of conceiving a female fetus is substantially enhanced by promoting ovulation in a fertile female mammal with an ovulation-inducing agent and artificially inseminating the female mammal during the period of expected ovulation with a sperm fraction of enhanced sperm motility from which immotile sperm and non-sperm seminal components have been separated and which is suspended in serum albumin or like physiologically acceptable vehicle.

11 Claims, No Drawings

METHOD OF INCREASING THE INCIDENCE OF FEMALE OFFSPRING

BACKGROUND OF THE INVENTION

This invention relates to methods for increasing the incidence of females in the offspring of mammals, especially humans.

In mammals, the sex is determined by two different types of sperm, which have either an X-chromosome (X-sperm) or Y-chromosome (Y-sperm). Fertilization with Y-sperm produces males. The assumption that these two kinds of sperm differ in size and weight has led to a series of investigations, in which the separation of the X- and Y-sperm has been attempted by sedimentation, centrifuging, electrophoresis, variation in pH-value or flotation. See, e.g., U. S. Pat. No. 3,687,806; Schilling, Erich, J. Reprod. Fert. (1966) 11, 469–472; Chem. Abstr. 66, 44818q (1967); A. M. Roberts, Nature, Vol. 238, pp. 223–225 (1972) ; Lang, J. L., Chemtech, March, 1973, pp. 190–192; Symposium, "Sex Ratio at Birth—Prospects for Control," American Soc. of Animal Sci., July 31-Aug. 1, 1970; Beatty, R. A., Bibliography (With Review) Reproduction Research Information Service, Ltd., Biblphy. Reprod. 23:1, Jan. 1974.

In U.S. Pat. No. 4,009,260, I claim methods for increasing the incidence of males in the offspring of mammals by artificially inseminating a fertile female with a Y-sperm enriched sperm fraction of that mammal obtained by maintaining at least the sperm portion of progressively motile sperm-containing semen, either as such or suspended in an aqueous suspending vehicle physiologically acceptable to the sperm, as an upper layer in vertical interfacial contact, at a temperature at which the motile sperm are motile, with a lower discrete layer of a first aqueous contacting medium physiologicaly acceptable to the sperm and in which the motile sperm migrate downwardly at a slower rate than in the upper layer, until a portion only of the motile sperm of the semen having migrated downwardly into the contacting medium, thereby producing a contacting medium containing a higher proportion of Y to X sperm than in the starting sperm, and repeating the step at least once, employing in the upper layer the motile sperm which have migrated to the first aqueous contacting medium and as the lower layer of second aqueous contacting medium physiologically acceptable to the sperm and in which the motile sperm migrate downwardly at a slower rate than in the first contacting medium.

In U.S. Pat. No. 4,007,087, I claim a method for enhancing the survival rate of sperm subjected to frozen storage by subjecting sperm to the above-described process prior to freezing.

The process of U.S. Pat. No. 4,009,260 relies upon enrichment of the Y-sperm in the motile sperm-fractionation process to increase the incidence of conception of male offspring. Unfortunately, the process cannot be used to produce an X-sperm-enriched sperm fraction.

The importance of a method of increasing the incidence of female offspring is obvious. In milk cows, female calves are always preferred, except when a breeding bull is desired. In racing horses, mares are often preferred over stallions. Many humans desire or would prefer girls as progeny.

E. Adashi et al., reporting in Fertility & Sterility, 31, No. 6, 620–626 (1979) noted a sex ratio (female/male) of 1.3–1.4 in the offspring of women in whom ovulation was induced with clomiphene ("Clomid," Merrell-Dow). However, L. Klay, Fertility & Sterility, Vol. 27, No. 4, April 1976, reported 11 males and 6 female births in women on clomiphene-regulated ovulation. William H. James, British Medical Journal, Vol. 281, p. 711, 1980 reported that female offspring is more likely to be born than male following both clomiphene and gonadotrophin administration. However, the percentage of female offspring (56–57%) is not high enough to render such therapy a predictable method of producing female offspring.

I have found that, surprisingly, in accordance with this invention that the incidence of female offspring which are conceived by women in whom ovulation has been artificially induced can be markedly increased, even in women artificially inseminated with a Y-sperm enriched sperm fraction.

SUMMARY OF THE INVENTION

This invention is a method for promoting the conception of a female fetus in a female mammal for whom a female offspring is desired, which comprises the steps of inducing ovulation in the mammal with an ovulation inducing agent and artificially inseminating the female mammal proximate the time of ovulation with a motile sperm enriched fraction of sperm of that mammal from which immotile sperm and non-sperm components of the semen have been separated and which is suspended in a liquid vehicle which is physiologically acceptable to the sperm.

DETAILED DISCUSSION

My invention is based upon my discovery that in some sex preselection clinics where my patented method for increasing the incidence of male offspring was practiced on females desiring a male offspring, the incidence of female offspring conceived was higher than in other clinics. In analyzing the clinical data, I determined that in vertually all cases where the female offspring was produced, ovulation in the mother had been induced with clomiphene. For example, in clinics where women were artificially inseminated with a highly Y-sperm enriched (ca. 75%) sperm fraction produced according to the three-step (2.5 hours process of U.S. Pat. No. 4,009,260, the females who were on clomiphene therapy conceived seven females and one male, notwithstanding the fact that they were impregnated with sperm that was predominantly (ca. 75%) male producing Y-sperm. In contradistinction, the mothers who were not on such therapy conceived 18 males and only 2 females, when artificially impregnated with sperm which had been Y-enriched by the same method. I found this pattern existed in other sex preselection clinics. Of 57 offspring conceived by women cervically artificially inseminated with a Y-sperm enriched sperm fraction, 8 females and only 3 males were conceived by women on clomiphene therapy whereas 36 males and only 10 females were conceived by women not on clomiphene therapy who were similarly artificially inseminated. Surprisingly, almost all females conceived by women on clomiphene therapy, were conceived by women who had been inseminated with a Y-sperm enriched sperm fraction.

In two infertility clinics where women were cervically artificially impregnated with motile sperm enriched but not highly Y-sperm enriched sperm fraction produced according to my patented process, 4 of the 5 offspring conceived by women in which ovulation was induced with clomiphene were girls, in contradistinction to an overall production of 17 males and 16 females in such clinics in women artificially inseminated with such a sperm fraction.

The overwhelming predominance of female offspring in women in whom ovulation was induced with clomiphene appears to be the result of an interaction between the effects of the clomiphene and the characteristics of the sperm which are present in a motile sperm-enriched isolated sperm fraction. Although clomiphene itself appears to alter somewhat the male/female ratio of offspring, it does not alter that ratio overwhelmingly in favor of females with such predictability in women who conceive after sexual intercourse.

There are several explanations why conception by artificial insemination with a motile sperm-enriched and even with a Y-sperm enriched sperm fraction usually produces a female rather than a male child. One such explanation is that the Y-sperm present in a Y-sperm enriched sperm fraction produced according to my patented process, although highly motile, have a shortened period of fertility, as reported by Z. Binor et al., Abstracts, 37th Annual Meeting, Mar. 17-18, 1981, Fertility & Sterility, February, 1981, page 242. Although the Y-sperm is predominant in such a fraction, if their period of fertility is shorter than the time required for the sperm to reach the ovum, the X-sperm may predominate in the pool of fertile sperm at the time of conception.

Another possible explanation is that the high motility of the Y-sperm cause them to exhaust their energy pool in the clomiphene-altered cervical mucus before reaching the situs of the ovum. This also would cause the X-sperm to predominate in the population of fertile sperm at the time of conception, even though the Y-sperm predominated in the starting sperm fraction.

A third possible explanation is that the estrogenic properties of clomiphene alters the female's reproductive tract so as to be more receptive to X-sperm than to Y-sperm. This fact, coupled with shorter period of fertility of the Y-sperm in the Y-sperm enriched sperm fraction, compared to that of the sperm present in the original semen, renders conception by a Y-sperm statistically improbable notwithstanding their higher numbers compared to the X-sperm present therein.

Whatever the explanation, the increase in the incidence of female offspring in women in whom ovulation is induced with clomiphene and artificially inseminated with a motile sperm enriched sperm fraction suspended in serum albumin or the like is dramatic and exceeds substantially the incidence of female offspring conceived by such women by sexual intercourse.

Although the foregoing discussion relates to human beings, the process of this invention can be practiced with other species of mammals, e.g., bovine and equine. Similarly, although ovulation is preferably induced with clomiphene, other ovulating inducing agents, such as gonadotrophins can be employed, e.g., HCG ("Pregnyl," Organon), HMG ("Pergonal," Serono) and bromocriphinemesylate ("Parlodel," Sandoz). Preferred are those which, like clomiphene, increase the viscosity of the cervical mucosa.

The sperm fraction employed for artificial insemination is motile sperm enriched. Surprisingly, such sperm enriched fraction can also be Y-sperm enriched, e.g., so that the sperm are 75% or more Y-sperm, without adversely affecting the desired objective of conception of a female fetus. Both types of sperm fractions can be produced according to the process of U.S. Pat. No. 4,009,260, whose disclosure is incorporated herein by reference. To produce a motile sperm enriched fraction, the starting semen from a fresh ejaculate is suspended in a suspending vehicle physiologically acceptable to the sperm, e.g., isotonic or Tyrode solution, and preferably then separated from the seminal fluid, e.g., by centrifugation. The sperm, preferably suspended in fresh suspending vehicle, is then layered onto the top of a column of an aqueous contacting medium which is physiologically acceptable to the sperm and which retards the migration rate of the sperm, e.g., Tyrode solution containing serum albumin. When a significant number of motile sperm have migrated into the lower layer, it is separated from the upper layer. Because only motile sperm can migrate downwardly into the lower layer, the sperm fraction recovered in the lower layer is enriched in motile sperm compared to the sperm in the starting semen. If the fractionation process is terminated before the majority of the motile sperm have migrated into the lower layer, some Y-sperm enhancement, e.g., to 55-65%, can occur.

To produce a sperm fraction which is substantially enriched in Y-sperm, the above-described fractionation is repeated with the thus-obtained sperm fraction and a second contacting medium which retards migration rate more than the first contacting medium, which further enhances the Y-sperm content of the sperm migrating thereto, so that sperm fractions having a 70-90% or more Y-sperm content can be obtained.

Examples of aqueous solutions which are physiologically acceptable to the sperm and can thus be used as suspending vehicles and contacting media are well known in the art and include solutions such as for example, Tyrode solution, Ringer solution, Hanks' solution, isotonic sodium chloride solutions, Medium 199, Eagle's Medium, egg yoke-TRIS extender, etc. The density and/or viscosity of these solutions can be increased by the addition thereto of an additive described hereinafter which can be present in the contacting medium.

The contacting medium can be entirely different in composition from the aqueous suspending vehicle, so long as both are physiologically acceptable to the sperm. However, they can be and preferably are essentially the same solutions, e.g., Tyrode solution, with the contacting medium containing an additional ingredient or a larger amount of a common ingredient, which retards significantly the migration rate of the motile sperm compared to their settling rate in the suspending vehicle. As stated above, such an ingredient ordinarily increases both the density and the viscosity of the contacting medium.

Aqueous contacting media which retard the migration rate of motile semen compared to the suspending vehicle generally have significantly higher densities and viscosities than water, isotonic saline solutions, Tyrode solution and other solutions suitable as suspending vehicles. It is theoretically possible to increase the density of the contacting medium without simultaneously significantly increasing its viscosity. Similarly, polymers which form a sol or gel can greatly increase viscosity and have little effect upon density. However, as a practical matter a contacting medium which retards migration rate and is physiologically acceptable to the sperm generally has both higher density and viscosity than a suspending vehicle which does not retard migration rate. In any event, whether the lowering of the migration rate of the motile sperm in the contacting medium is the result of the latter's higher density, higher viscosity, or both, is not critical as long as the migration rate of the motile sperm is reduced.

As stated above, the contacting medium, in addition to retarding the migration rate of the sperm, should meet the criteria mentioned above for the suspending vehicle of low density in which the sperm may be dispersed, i.e., it must by physiologically acceptable to the sperm. Thus, there may be employed any physiologically acceptable solution in which sperm can be maintained in a viable and motile state, for example, those mentioned above as suspending vehicles, which are adapted by means of soluble materials known to pharmacologists and physiologists to the desired condition of higher density and/or viscosity. Such additives include, for example, salts, low molecular and high molecular weight organic compounds, e.g., mono- and oligo-saccharides, aminoacids, peptides, proteins and proteids, e.g., egg yolk, and synthetic polymers, for example, polyvinylpyrrolidone. Of the foregoing additives, proteins, e.g., globulins and albumins, especially serum albumin or ovalbumin, and most preferably human serum albumin, are preferred.

In carrying out the method of this invention, ovulation is induced in a female for whom a female offspring is desired, preferably with clomiphene or like ovulation inducing agent which increases the viscosity of cervical mucous. As stated above, this increase in viscosity may be responsible for the more motile Y-sperm exhausting their energy pool before reaching the ovum. The dosage regimen will depend on the selected ovulation inducing agent. In the case of clomiphene citrate ("Clomid"), the conventional dosage is 250-500 mg./month, preferably given in divided dosages of 50-100 mg./day on the 5th through the 9th days after menstruation.

Artificial insemination is preferably conducted by injecting the sperm fraction directly into the cervical cavity, e.g., with a semen specimen in a final volume ranging between 0.5 and 1.0 ml. injected into the cervical canal at the level of the internal cervical os. See, Dmowski, W. P. et al., Use of Albumin Gradients for X and Y Sperm Separation and Clinical Experience With Male Sex Preselection, Fert. and Steril., 31:52, 1979.

The impregnation is preferably conducted within 24 hours and more preferably with 12 hours and most preferably within 6 hours of the ejaculation of the sperm from which the motile sperm-enriched fraction is obtained, preferably keeping the sperm at all times below 40° C., preferably about 20°-25° C. If desired, the insemination can be repeated at different times of the same day or on successive days with aliquots of the same sperm fraction or like sperm fractions obtained from separate ejaculates.

The selectivity of the process of this invention can be further enhanced by suspending the fractionated sperm in a suspending vehicle which contains a female sex hormone, preferably steroidal, e.g., conjugated estrogens, estrone, ethinyl estradiol, 3-cyclopentyloxyether of ethinyl estradiol, estradiol, polyestradiol phosphate, preferably at low concentration, e.g., a few micrograms per milliliter.

Not only does the process of this invention increase substantially the incidence of females in the offspring conceived, the incidence of spontaneous abortion is lower than that experienced by the human females generally.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. For example, it is contemplated that this invention can be conducted on a multiplicity of female mammalian species including but not limited to: bovine, equine, porcine, ovine, canine.

EXAMPLE

In sex selection artificial insemination clinics, sperm from a male donor was fractionated by one of the following methods:

Protocol I

Suspend a fresh ejaculate from a fertile human male in Tyrode solution (1:1 vol/ratio); centrifuge; separate the thusproduced sperm pellet from the supernatant and re-suspend in an amount of fresh Tyrode solution which results in 20-80 million sperm per milliliter in the suspension. Layer the suspension (0.5 ml.) onto a column of 6-10% human serum albumin (hsa), incubate at 20°-25° C. and after one hour separate the hsa layer (pipette) from the column centrifuge and re-suspend in Tyrodes solution for artificial insemination.

Protocol II

Follow Protocol I, except layer the sperm suspension onto a two-layered column of hsa, the top layer of which is 1.0 ml. of 7.5-10% hsa and the bottom layer of which is 0.5 ml. of 17.5-20% hsa. After incubation for one hour, separate the sperm layer and 30 minutes thereafter remove the bottom layer of the column (pipette), centrifuge and re-suspend in Tyrodes solution for artificial insemination.

Protocol III

Follow the procedure of Protocol I, except use a 6% solution of hsa and after one hour at 20°-25° C., remove (pipette) the hsa layer of the column, layer it onto the top of a two-layer column of hsa solution, the top layer of which is 1 ml. of 10-12% hsa and the bottom layer of which is 0.5 ml. of 20% hsa. After one hour at 20°-25° C., separate the 20% hsa layer (pipette), centrifuge and re-suspend in Tyrodes solution for artificial insemination.

The results of pregnancies achieved by the cervical artificial insemination according to the method of Dmowski, described above, using the above-obtained Y-sperm enriched sperm fractions, of fertile females previously given the daily amount of Clomid ® brand of clomiphene shown in Table I on each of the 5th through 9th days after menstruation, is shown in Table I.

TABLE I

PREGNANCY RESULTS WHEN CLOMIPHENE IS USED TO REGULATE OR INDUCE OVULATION IN CONJUNCTION WITH PROTOCOL II & III (SEX SELECTION) OR PROTOCOL I (INFERTILITY) SPERM FRACTIONATION

| Age of Female Patient | Clomiphene Mg. | Cycles* | Sperm for A.I. No. × $10^6$ | Motility | Fractionation Protocol | Offspring Female | Male |
|---|---|---|---|---|---|---|---|
| 27 | 50 | (1-4) | 10 | 95% 3+ | III | x | |
| 28 | 50 | (1-10) | 10-15 | 100% 3+ | III | x | |
| 31 | 50 | (1-1) | 40-50 | 95% 4+ | III | | x |
| 33 | 50 | (1-4) | 14 | 90% 3+ | III | x | |
| 37 | 150 | (8-8) | 5 | 95% 3+ | III | 2** | |
| 27 | 50 | (1-1) | 100 | 90% 3+ | I | x | |
| 29 | 50 | (3-1) | 30 | 80% 4+ | I | x | |
| 35 | 150 | (5-13) | 14 | 46% | II | x | |
| 28 | 50 | (1-1) | 8 | 78% | II | | x |
| 31 | 50 | (4-4) | 45 | 91% | II | | x |
| 29 | 150 | (2-2) | 6 | 85% | I | x | |
| 30 | 100 | (2-3) | 40 | 77% | I | x | x |
| | 50 | | | | III | x | |
| | 50 | | | | III | x | |
| | | | | | | 12 | 4 |

*Number of cycles on Clomid - number of cycles required to conceive
**Dizygotic females The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for promoting the conception of a female fetus in a fertile female mammal for whom a female offspring is desired, which comprises the steps of inducing ovulation in the female mammal with an ovulation inducing agent and thereafter artificially inseminating the female mammal proximate the time of ovulation with a motile sperm enriched fraction of sperm of that mammal from which immotile sperm and non-sperm components of the semen have been separated and which is suspended in a liquid vehicle which is physiologically acceptable to the sperm.

2. A method according to claim 1 wherein the mammal is a human being.

3. A method according to claim 2 wherein the human being is inseminated cervically.

4. A method according to claim 1 wherein the ovulation inducing agent is clomiphene.

5. A method according to claim 1 wherein the ovulation inducing agent is gonadotrophin.

6. A method according to claim 1 wherein the suspending liquid vehicle is an aqueous solution of human serum albumin.

7. A method according to claim 1 wherein the sperm is enriched in Y-sperm.

8. A method according to claim 1 wherein the mammal is a human being and is cervically inseminated with sperm which is enriched in Y-sperm.

9. A method according to claim 8 wherein the ovulation inducing agent is clomiphene.

10. A method according to claim 1 wherein the liquid vehicle is an aqueous solution of human serum albumin.

11. A method according to claim 1 wherein the mammal is a bovine.

* * * * *